United States Patent [19]
Scott et al.

[11] Patent Number: 5,582,814
[45] Date of Patent: Dec. 10, 1996

[54] 1-(P-N-BUTYLBENZYL) DTPA FOR MAGNETIC RESONANCE IMAGING

[75] Inventors: Daniel M. Scott, Waltham; Randall B. Lauffer, Brookline, both of Mass.

[73] Assignee: Metasyn, Inc., Cambridge, Mass.

[21] Appl. No.: 227,961

[22] Filed: Apr. 15, 1994

[51] Int. Cl.$^6$ .............. A61K 49/04; C07F 5/00; C07F 13/00; C07F 15/00
[52] U.S. Cl. .............. 424/9.364; 534/16; 556/50; 556/63; 556/107; 556/117; 556/134; 556/148; 562/489; 128/653.4; 436/173
[58] Field of Search .............. 424/9, 9.364; 534/16; 556/50, 63, 107, 117, 134, 148; 562/489; 128/653.4, 654; 436/173

[56] References Cited

U.S. PATENT DOCUMENTS

| | | | |
|---|---|---|---|
| 3,632,637 | 1/1972 | Martell | 260/519 |
| 4,150,047 | 4/1979 | Coe et al. | 260/439 R |
| 4,308,249 | 12/1981 | Frank et al. | 424/1 |
| 4,331,647 | 5/1982 | Goldenberg | 424/1 |
| 4,352,751 | 10/1982 | Wieder et al. | 260/112 R |
| 4,361,544 | 11/1982 | Goldenberg | 424/1 |
| 4,401,647 | 8/1983 | Krohn et al. | 424/1.5 |
| 4,472,509 | 9/1984 | Gansow et al. | 436/548 |
| 4,615,879 | 10/1986 | Runge et al. | 424/9 |
| 4,639,365 | 1/1987 | Sherry | 424/9.363 |
| 4,647,447 | 3/1987 | Gries et al. | 424/9 |
| 4,687,658 | 8/1987 | Quay | 424/9 |
| 4,714,607 | 12/1987 | Klaveness | 424/9 |
| 4,746,507 | 5/1988 | Quay | 424/9 |
| 4,834,964 | 5/1989 | Rosen | 424/9 |
| 4,859,451 | 8/1989 | Quay et al. | 424/9 |
| 4,880,008 | 11/1989 | Lauffer | 128/654 |
| 4,885,363 | 12/1989 | Tweedle et al. | 424/9.363 |
| 4,899,755 | 2/1990 | Lauffer et al. | 128/654 |
| 4,957,939 | 9/1990 | Gries et al. | 424/9 |
| 4,963,344 | 10/1990 | Gries et al. | 424/9 |
| 4,980,502 | 12/1990 | Felder et al. | 562/444 |
| 5,078,986 | 1/1992 | Bosworth et al. | 424/9 |
| 5,250,285 | 10/1993 | Lauffer et al. | 424/9 |
| 5,318,771 | 6/1994 | Lauffer et al. | 424/9 |
| 5,362,475 | 11/1994 | Gries et al. | 424/9 |

FOREIGN PATENT DOCUMENTS

| | | |
|---|---|---|
| 8633082 | 1/1983 | Australia . |
| 0133603 | 2/1985 | European Pat. Off. . |
| 0165728 | 12/1985 | European Pat. Off. . |
| 169299 | 1/1986 | European Pat. Off. . |
| 0250358 | 6/1986 | European Pat. Off. . |
| 0232751 | 8/1987 | European Pat. Off. . |
| 0230893 | 8/1987 | European Pat. Off. . |
| 0258616 | 3/1988 | European Pat. Off. . |
| 0304780 | 8/1988 | European Pat. Off. . |
| 0290041 | 11/1988 | European Pat. Off. . |
| 0290047 | 11/1988 | European Pat. Off. . |
| 0292761 | 11/1988 | European Pat. Off. . |
| 0292689 | 11/1988 | European Pat. Off. . |
| 0331616 | 2/1989 | European Pat. Off. . |
| 374947 | 6/1990 | European Pat. Off. . |

(List continued on next page.)

OTHER PUBLICATIONS

Bagley et al., "Distribution of Intravenously Administered Ferrioxamine–59 and Ferric N,N'-Ethylenebis (α Imino–2–Hydroxy–5–Chlorophenylacetate) in Rats", *Proc. Soc. Exptl. Biol. Med.*, 127, pp. 798–801 (1968).

Brasch et al., "Contrast–Enhanced NMR Imaging: Animal Studies Using Gadolinium–DTPA Complex", *AJR*, pp. 625–630 (1984).

Brittain et al., "Luminescence and NMR Studies of the Conformational Isomers of Lanthanide Complexes with an Optically Active Polyaza Polycarboxylic Macrocycle," *Inorg. Chem.*, 23, pp. 4459–4466 (1984).

(List continued on next page.)

*Primary Examiner*—Gary E. Hollinden
*Attorney, Agent, or Firm*—Fish & Neave; James F. Haley, Jr.; Pablo D. Hendler

[57] ABSTRACT

Paramagnetic metal complexes of 1-(p-n-butylbenzyl)diethylenetriamine pentaacetic acid and pharmaceutically acceptable salts thereof are effective as tissue-specific MRI contrast agents, and in particular as hepatobiliary MRI contrast agents.

15 Claims, 3 Drawing Sheets

FOREIGN PATENT DOCUMENTS

| | | |
|---|---|---|
| 0405704 | 1/1991 | European Pat. Off. . |
| 0450742 | 10/1991 | European Pat. Off. . |
| 0454078 | 10/1991 | European Pat. Off. . |
| 463644 | 1/1992 | European Pat. Off. . |
| 2354993 | 1/1978 | France . |
| 2643370 | 8/1990 | France . |
| 2606721 | 9/1976 | Germany . |
| 3129906 | 2/1983 | Germany . |
| 3401052 | 7/1984 | Germany . |
| WO-A-85/05554 | 12/1985 | WIPO . |
| WO-A-86/01410 | 3/1986 | WIPO . |
| WO-A-86/02005 | 4/1986 | WIPO . |
| WO-A-86/02352 | 4/1986 | WIPO . |
| WO-A-86/02841 | 5/1986 | WIPO . |
| WO-A-86/06605 | 11/1986 | WIPO . |
| 88/07521 | 10/1988 | WIPO . |
| WO-A-89/01476 | 2/1989 | WIPO . |
| WO-A-89/01475 | 2/1989 | WIPO . |
| WO-A-89/12631 | 12/1989 | WIPO . |
| WO-A-90/03804 | 4/1990 | WIPO . |
| WO-A-91/03200 | 3/1991 | WIPO . |

OTHER PUBLICATIONS

Chen et al., "Paramagnetic Metalloporphyrins as Potential Contrast Agents in NMR Imaging", FEBS Letters, 168, pp. 70–74 (1984).

Davison, "Protein Binding", Fundamentals of Drug Metabolism and Drug Disposition, La Du et al., eds., R. E. Krieger Pub. Co., Malabar, Fla., pp. 63–75 (1971).

Desreux et al., "Nuclear Magnatic Resonance Spectroscopy of Lanthanide Complexes with a Tetraacetic Tetraaza Macrocycle. Unusual Conformation Properties", Inorg. Chem., 19, pp. 1319–1324 (1980).

Felix et al., "Brain Tumors MR Imaging with Gadolinium–DTPA", Radiology, 156, pp. 681–688 (1985).

Graf et al., "Iron–catalyzed Hydroxyl Radical Formation", J. Biol. Chem., 259, pp. 3620–3624 (1984).

Haddock et al., "Biliary Excretion of Chelated Iron", Proc. Soc. Exptl. Biol. Med., 120, pp. 663–668 (1965).

Konishiroku Photo Industry Co., Ltd., "Processing of Silver Halide Color Photographic Material", Chemical Abstracts, 101, p. 537, Abstract No. 219677p (1984).

Krishnamurthy et al., "Technetium–99m–Iminodiacetic Acid Organic Anions: Review of Biokinetics and Clinical Application in Hepatology", Hepatology, 9, pp. 139–153 (1989).

Lauffer et al., "Stereospecific Binding of rac–Iron(III) N,N'–Ethylenebis[(5–bromo–2–hydroxyphenyl)glycinate)]to the Bilrubin Site on Human Serum Ablumin, " J.A.C.S., 109, pp. 2216–2218 (1987).

Lauffer et al., "Albumin Binding of Paramagnetic Hepatobiliary Contrast Agents: Enhancement of Outer Sphere Relaxivity", Nucl. Med. Biol., 15, pp. 45–46 (1988).

Lauffer et al., "Iron–EHPG as an Hepatobiliary MR Contrast Agent: Initial Imaging and Biodistribution Studies", J. Comp. Assist. Tomog., 9, pp. 431–438 (1985).

Lauffer et al., "Hepatobiliary MR Contrast Agents: 5–Substituted Iron–EHPG Derivatives", Magn. Res. Med., 4, pp. 582–590 (1987).

Lauffer et al., "Preparation and Water Relaxation Properties of Proteins Labeled with Paramagnetic Metal Chelates", Magn. Res. Imaging, 3, pp. 11–16 (1985).

Lauffer, "Paramagnetic Metal Complexes as Water Proton Relaxation Agents for NMR Imaging: Theory and Design," Chem. Rev., 87, pp. 901–927 (1987).

Levi et al., "Two Hepatic Cytoplasmic Protein Fractions, Y and Z, and Their Possible Role in the Hepatic Uptake of Bilirubin, Sulfobromophthalein, and Other Anions", J. Clin. Invest., 48, pp. 2156–2167 (1969).

Martell et al., "Development of Iron Chelators for Cooley's Anemia," Inorganica Chimica Acta, 138, pp. 215–230 (1987).

Martell, "The Design and Synthesis of Chelating Agents", Development of Iron Chelators for Clinical Use, Martell et al., eds., Elsevier North Holland, Inc., pp. 65–104 (1981).

McCandlish et al., "Comparison of the Structures and Aqueous Solutions of [o–Phenylenediaminetetraacetato (4–)] cobalt (II) and [Ethylenediaminetetraacetato (4–1)] cobalt (II) Ions", Inorg. Chem., 17, pp. 1383–1394 (1978).

Moerlein et al., "The Chemistry of Gallium and Indium as Related to Radiopharmaceutical Production", In. J. Nucl. Med. Biol., 8, pp. 277–287 (1981).

Moore et al., "Synthesis, Characterization, and Solid–State Structure of a New Hexachelating Ligand and Its Complex with Gallium(III)," Inorg. Chem., 28, pp. 1504–1506 (1989).

Motekaitis et al., "New Synthetic,Selective, High–Affinity Ligands for Effective Trivalent Metal Ion Binding and Transport", Inorganica Chimica Acta, 198–200, pp. 421–428 (1992).

Pecoraro et al., "Gallium and Indium Imaging Agents. 2. Complexes of Sulfonated Catechoylamide Sequestering Agents", Inorg. Chem., 21, pp. 2209–2115 (1982).

"Phenolic derivatices of (hydroxyalkyl)alky=–lenediamineacetic acids and their salts", Chemical Abstracts, 89, p. 561, Abstract No. 215057x (1978).

Rocklage et al., "Manganese(II) N,N'–Dipyridoxyl–ethylenediamine–N,N'–diacetate 5,5'–Bis(phosphate). Synthesis and Characterization of a Paramagnetic Chelate for Magnetic Resonance Imaging Enhancement", Inorg. Chem., 28, pp. 477–485 (1989).

Rocklage et al., "Structural and Thermodynamic Characterization of Manganese(II) N,N'Dipyridoxyl–ethylendiamine–N,N'–diacetate. A Novel Manganese(II) Chelate", Inorg. Chem., 27, pp. 3530–3534 (1988).

Sun et al., "Synthesis of Multidentate Ligands Containing Hydroxypyridyl Donor Groups," Tetrahedron, 47, pp. 357–364 (1991).

Taliaferro et al., "New Multidentate Ligands. XXIV. Disodium–N,N'bis(2–hydroxy–5–sulfobenzyl)ethylenediamine–diacetic acid, a new chelating ligand for trivalent metal ions", Chemical Abstracts, 101, p. 369, Abstract No. 44224j (1984).

Taliaferro et al., "New Multidentate Ligands. 22. N,N'–Dipyridoxylethylenediamine–N,N' diacetic Acid: A New Chelating Ligand for Trivalent Metal Ions", Inorg. Chem., 23, pp. 1188–1192 (1984).

Taliaferro et al., "New Multidentate Ligands. XXIV, Disodium-N, N'-bis(2-hydroxy-5-sulfobenzyl)-ethylenediaminediacetic Acid, a New Chelating Ligand for Trivalent Metal Ions", *Inorganica Chimicia Acta*, 85, pp. 9–15 (1984).

Theodorakis et al., "Localization of Technetium 99m-Ethylenediamine-N,N'-bis [(α-2-hydroxy-5-bromophenyl) acetic Acid and Technetium 99m-N-] 2-Mercapto-1-oxopropyl) glycine in Hepatobiliary System", *J. Pharm. Sci.*, 69, pp. 581–584 (1980).

Unger et al., "Magnetic Resonance Imaging Using Gadolinium-Labeled Monoclonal Antibody," *Invest. Radiology*, 20, pp. 693–700 (1985).

Weinmann et al., "Characteristics of Gadolinium-DTPA Complex: A Potential NMR Contrast Agent", *AJR*, 142, pp. 619–624 (1984).

Yeh et al., "A New Route to 'Bifunctional' Chelating Agents: Conversion of Amino Acids to Analogs of Ethylenedinitrilo-tetraacetic Acid", *Anal. Biochem.*, 100, pp. 152–159 (1979).

Martell et al., "Critical Stability Constants vol. 1, Amino Acids," pp. 124–125, 135, Plenum Press, New York (1974).

1-(P-N-BUTYLBENZYL) DTPA FOR MAGNETIC RESONANCE IMAGING

TECHNICAL FIELD OF THE INVENTION

The present invention relates to diagnostic nuclear magnetic resonance imaging (MRI or MR imaging). In particular, this invention relates to novel compounds that upon administration to a patient, can enhance the contrast in images of the patient's organs and tissue obtained through MRI. This invention also relates to pharmaceutical compositions comprising these compounds and to methods of making and using the compounds and compositions for MRI contrast enhancement.

BACKGROUND OF THE INVENTION

Nuclear magnetic resonance imaging (MRI) is one of the most useful diagnostic tools in medicine today. The technique is based on the discovery that atomic nuclei possess a magnetic moment which can be detected using a magnetic field. When placed in a magnetic field, nuclei arrange themselves in a manner that aligns their magnetic moments either with or against the direction of the magnetic field. Those that align against the field (so-called β-spin nuclei) are higher in energy than those aligned with the field (so-called α-spin nuclei). The energy difference between α- and β-spin nuclei is directly proportional to the strength of the applied field. To measure this difference in energy, the nuclei are subjected to electromagnetic radiation. Low energy α-spin nuclei absorb electromagnetic radiation causing them to "flip" against the field (or out of alignment with the field) into a high energy β-spin. The frequency of the absorbed radiation, known as the "resonance frequency," reveals the α-β energy difference. Alternatively, high energy β-spin nuclei or non-aligned nuclei may "relax" into a low energy α-spin state with concomitant release of electromagnetic radiation. Both the resonance frequency and the relaxation rates (measured in terms of relaxation rate ($1/T_1$) wherein $T_1$=the time that it takes for non-aligned nuclei to relax) for any nucleus is dependent on the magnetic environment surrounding that nucleus. For example, nuclei within a substantial (strong) electron shell are shielded from external magnetic fields and as a result possess a smaller α-β energy difference, compared to nuclei within a weak electron shell. Also, nuclei situated in the proximity of other paramagnetic nuclei relax faster and have higher relaxation rates than those for which such a relaxation mechanism is not available.

It is the difference in the nuclear magnetic relaxation rates of water protons that is most commonly used as the source of information in diagnostic MRI. Water is ubiquitously found in soft tissue. The hydrogen atoms in water possess paramagnetic nuclei (protons) that, when subjected to resonance frequency and relaxation-rate measurements, provide direct information regarding their physical microenvironment. The information can then be processed through computational techniques to obtain detailed anatomical images. Inspection of these images can reveal the presence of diseased or abnormal tissue, lesions and fractures or other malfunctions that may be present.

Not surprisingly, MR imaging of some tissue is more difficult than others. This may be due to any number of factors which result in low contrast and hence lack of resolution in the MR images obtained. Previous efforts to overcome such problems have led to the discovery of so-called contrast enhancement agents. Typically, such agents contain a paramagnetic metal ion which is capable of altering the relaxation rates of water protons in its proximity. Upon administration to a patient, the metal-containing contrast agent is absorbed by various organs depending on the patient's metabolic and excretion pathways. Once absorbed, the contrast agent alters the relaxation rates of water protons in the organ or tissue in which it resides. The MR images of that organ or tissue thus achieve enhanced contrast with respect to neighboring tissue which contains lower concentrations or none of the paramagnetic agent.

Because of the acute toxicity of most paramagnetic metals, however, ordinary inorganic salts of paramagnetic metals are unsatisfactory as contrast agents. A solution to this problem is to use an organic chelating ligand or metal-sequestering agent. Through complexation to the metal, the organic chelating ligand would prevent release of free, toxic metal yet allow proton relaxation enhancement by acting as a non-toxic paramagnetic carrier.

To be effective, MRI contrast agents (paramagnetic metal-ligand complexes) must satisfy several criteria. They must be stable and have high formation constants so that release of the toxic metal is prevented. They must be sufficiently soluble in aqueous solutions to facilitate their administration to a patient. And, they must be capable of efficient enhancement of relaxation rates of water protons in solution. Efficiency is generally measured in terms of "relaxivity" which is defined as the increase in relaxation rate per concentration of the paramagnetic complex measured in units of mM.

Gries et al. have described complexes for use as diagnostic agents in U.S. Pat. No. 4,647,447. Also, the active paramagnetic ingredient of the FDA-approved MRI contrast agent Magnevist® is a complex of diethylenetriaminepentacetic acid and gadolinium (III). In U.S. Pat. No. 4,899,755, Lauffer and Brady describe how paramagnetic metal-ligand complexes can be designed and synthesized to target specific tissue for MRI enhancement. This tissue-specific approach provides several improvements over the previously reported non-specific methods. Qualitatively, tissue-specific agents provide better MR images of the targeted tissues such as the liver and the bile duct. Quantitatively, tissue-specific contrast agents can be used in lower concentrations to achieve image enhancements similar to that observed with non-specific agents at higher doses. Thus, previously undetectable (or difficult to detect) liver tumors or malfunctions in the biliary system can be detected using hepato-biliary-specific contrast agents.

Another improvement upon the non-specific methods of the art is provided in U.S. Pat. No. 4,880,008 where the relaxivity-enhancement of contrast agents is shown to improve upon noncovalent binding to specific tissue proteins. This strategy not only allows targeting of specific tissue containing the binding proteins, it also provides image enhancement at even lower doses than previously possible (due to improved relaxivity enhancement of the protein-bound agents).

In spite of these advances, there remains a need for MRI contrast agents that combine favorable stability, solubility, relaxivity-enhancement and protein-binding characteristics with a tissue-specific pharmaco-kinetic profile.

SUMMARY OF THE INVENTION

The present invention provides improved compounds that are useful as tissue-specific MRI contrast agents, compositions containing those compounds and methods for using them. In particular, the present invention provides paramagnetic metal complexes of 1-(p-n-butylbenzyl)diethylenetriamine pentaacetic acid and pharmaceutically acceptable salts thereof as useful and efficient agents for improved tissue-specific enhancement of contrast in MRI of mammalian organs and tissues.

DETAILED DESCRIPTION OF THE INVENTION

The tissue-specific contrast agents of this invention comprise complexes of a paramagnetic metal and 1-(p-n-butylbenzyl)diethylenetriamine pentaacetic acid and pharmaceutically acceptable salts thereof. The stereochemistry at position 1 may be R or S, and the paramagnetic complex may be used in racemic or enantiomerically pure form. Preferred paramagnetic metals of this invention are selected from the group consisting of Gd(III), Fe(III), Mn(II and III), Cr(III), Cu(II), Dy(III), Tb(III), Ho(III), Er(III) and Eu(III). The most preferred paramagnetic metal is Gd(III).

Pharmaceutically acceptable salts of this invention include those derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium, magnesium and zinc salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained. The preferred salts of this invention are the N-methyl-D-glucamine, calcium and sodium salts.

The pharmaceutical compositions of this invention comprise any of the complexes of the present invention, or pharmaceutically acceptable salts thereof, together with any pharmaceutically acceptable carrier, adjuvant or vehicle.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, TRIS (tris(hydroxymethyl)aminomethane), partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropyleneblock polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as *Ph. Helv* or similar alcohol.

The compounds and pharmaceutical compositions of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term "parenteral" as used herein includes subcutaneous, intravenous, intramuscular, intra-articular, intrasynovial, intrasternal, intrathecal, intrahepatic, intralesional and intracranial injection or infusion techniques.

When administered orally, the pharmaceutical compositions of this invention may be administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, when administered in the form of suppositories for rectal administration, the pharmaceutical compositions of this invention may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

As noted before, the pharmaceutical compositions of this invention may also be administered topically, especially when the target of treatment includes areas or organs readily accessible by topical application, including the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

For administration by nasal aerosol or inhalation, the pharmaceutical compositions of this invention are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated, the sensitivity of the MR imaging instrument, the target tissue of the imaging experiment, the particular mode of administration and the intended effect of use. It should be understood, however, that a specific dosage regimen for any particular patient will depend upon a variety of factors, including the activity (induced relaxivity) of the specific agent employed, the age, body weight, general health, sex, diet, time of administration, rate of excretion, drug combination, and the judgment of the treating physician.

Dosage levels of between about 0.1 and about 1000 µmol/kg body weight per day, preferably between about 0.5 and about 300 µmol/kg body weight per day of the active ingredient compound are useful. A typical preparation will contain between about 1–1000 mM of the active complex. Preferably, such preparations contain between about 10–500 mM of the active complex.

To preserve shelf stability, to enhance the safety of the contrast agents and to prevent in vivo release of toxic metal (or ligand), according to one embodiment of this invention the compositions further contain a free organic ligand or an excess of 1-(p-n-butylbenzyl)diethylenetriamine pentaacetic acid and pharmaceutically acceptable salts of such ligands, for example, calcium, sodium and meglumine (N-methyl-D-glucamine) salts and combination salts such as a calcium sodium salt. The pharmaceutically acceptable compositions contain between 0–5% (molar ratio) of excess organic ligand or a pharmaceutically acceptable salt thereof, preferably 0–1%, and most preferably 0–0.5%. The use of compositions with an excess of a chelating ligand in diagnostic imaging has been disclosed in greater detail in International patent publication WO 90/03804, European patent publications EP-A-0463644 and EP-A-454078 and U.S. Pat. No. 5,078,986.

The tissue-specific contrast agents of this invention may be readily obtained using conventional techniques. Scheme 1 illustrates a representative example of a process for the preparation of gadolinium(III)-1-(p-n-butylbenzyl)diethylenetriamine pentaacetate dimeglumine salt (MS-264). It will be appreciated by those of skill in the art that the below synthetic processes are not intended as a comprehensive list of all means by which the contrast agents or the intermediates of this invention may be synthesized. Further methods or modifications of the below process will be evident to those of skill in the art.

Starting with 4-n-butylaniline, the process involves diazotization, followed by metal-catalyzed coupling with acrylonitrile or an equivalent (e.g., an alkyl ester of acrylic acid). The product is converted to p-n-butylphenylalanine which is then processed to obtain its ethylenediamine amide. Reduction of the amide to the amine using a known reducing agent, Scheme 1

-continued
Scheme 1 preferably borane-THF complex, provides the p-n-butylbenzyl derivative of diethylenetriamine. The nitrogen atoms in this compound are alkylated using an alkyl ester of bromoacetic acid such as t-butylbromoacetate to give, after ester hydrolysis, the desired organic ligand.

Complexation to the paramagnetic metal can be achieved using any of the well-known procedures in the art. Scheme 1 provides an example of such a procedure involving the reaction of the ligand with gadolinium oxide in the presence of N-methyl-D-glucamine. Similar procedures using other paramagnetic metal oxides or salts instead of $Gd_2O_3$ and other bases instead of N-methylglucamine provide further paramagnetic contrast agents of this invention.

Optically active contrast agents may also be prepared using, for example, optically active p-n-butylphenylalanine or using other optically active intermediates in the process illustrated in Scheme 1. Optically active intermediates can, in turn, come from resolution of a corresponding racemic mixture or from stereoselective synthesis. Methods for both resolution of racemic mixtures and stereoselective synthesis of optically active compounds are well known and require no further description here.

The contrast agents of this invention are surprisingly efficient and tissue-specific in MRI of mammalian tissue.

Thus, this invention provides a method for tissue-specific contrast enhancement of MR images of mammalian organs and tissues. In particular, the method allows for contrast enhancement of MR images of the hepatobiliary system. For example, MS-264, the preferred contrast agent of this invention, exhibits surprisingly superior liver and bile specificity relative to structurally similar contrast agents previously disclosed (see Examples section). MS-264 can also be used for tissue-specific imaging of tumors and the blood pool.

Following administration of the contrast agent, NMR imaging is carried out; the choice of pulse sequence (inversion recovery, IR; spin echo, SE; gradient echo, GE; turbo FLASH,; etc.) and the values of the imaging parameters (echo time, TE; inversion time, TI; repetition time, TR; flip angel, etc.) will be governed by the diagnostic information sought. In general, if one desires to measure $T_1$, then TE should be less than 30 milliseconds (or the minimum value) to maximize $T_1$-weighting. Conversely, if one desires to measure $T_2$, then TE should be greater than 30 milliseconds to minimize competing $T_1$ effects. TI and TR will remain approximately the same for both $T_1$- and $T_2$-weighted images; TI and TR are generally on the order of about 200–600 and 100–1000 milliseconds, respectively.

It is well known that ligands form complexes that are useful as MRI contrast agents may also be used in chelate complexes for diagnostic X-ray imaging. Therefore, according to another embodiment of this invention, metal complexes of 1-(p-n-butylbenzyl) diethylenetriamine pentaacetic acid and pharmaceutically acceptable salts thereof are used for diagnostic X-ray imaging.

In order that this invention may be more fully understood, the following examples are set forth. These examples are for the purpose of illustration only and are not to be construed as limiting the scope of the invention in any way.

EXAMPLES

Relaxivity in rat liver cytosol

Rat liver cytosol was prepared by homogenizing rat livers (25% w/v) in 0.25M sucrose/0.01M phosphate buffer, pH 7.4, centrifuging at 100,000 g for 90 min at 4° C., and concentrating the supernatant by pressure ultrafiltration to get the cytosol protein concentration close to that in vivo (5–10%). The relaxivity of the Gd(III) complexes in cytosol was measured at 37 ° C. using a Bruker 20MHz Minispec equipped with a variable temperature probe. The inversion-recovery pulse sequence with 10 data points was used for $T_1$ measurements. $1/T_1$ relaxation rates of solutions with varying concentrations of the chelates (0.01–0.5 mM) were determined. The limiting slope of the $1/T_1$ vs concentration plot at low concentrations of the chelates in units of $s^{-1}$ $mM^{-1}$ was taken as the relaxivity (R1) of the chelate in cytosol. Results are summarized in TABLE 1 (Bn=benzyl).

Higher relaxivity values imply higher binding affinity to cytosolic proteins and/or greater relaxivity when bound.

TABLE 1

Relaxivity in Rat Liver Cytosol

| DTPA derivative | R1 in liver cytosol 20 MHz, 37° C. ($s^{-1}$ $mM^{-1}$) |
|---|---|
| DTPA (R = R' = H) | 7.1 |
| BOPTA (R = H, R' = BnOCH$_2$) | 11.3 |
| R (R' = H) | |
| 1-(benzyl) | 11.7 |
| 2-(benzyl) | nd |
| 1-(phenylethyl) [CH$_2$CH$_2$Ph] | 13.6 |
| 1-(p-ethoxybenzyl) [EOB-DTPA] | 14.4 |
| 1-(p-ethylbenzyl) | 16.4 |
| 1-(p-isopropylbenzyl) | 18.7 |
| 1-(p-n-butylbenzyl) [MS-264] | 23.8 |
| 1-(2,4-di-Me-benzyl) | 15.3 |
| 1-(2,4,6-tri-Me-benzyl) | 17.9 |
| 1,3-dibenzyl | 23.7 |
| 1,4-dibenzyl | 20.0 |
| 1-(p-ethylbenzyl)-3-benzyl | nd |
| 1,3-di(p-ethylbenzyl) | nd |
| 1-(p-n-butylbenzyl)-3-benzyl | nd |

Rat liver uptake and $1/T_1$ relaxation rates of rat liver

Un-anesthetized adult male Sprague Dawley rats (200–300 g) were injected in the tail vein with 50 μmol/kg of gadolinium chelate labeled with $^{153}$Gd. Rats (approx. 3 per time period) were euthanized by cervical dislocation (while anesthetized by CO$_2$) at 1, 5 and 30 min. post-injection. The liver was analyzed for $^{153}$Gd concentration using a gamma counter. The percentage of the injected dose (% ID) in the liver was determined for each time point and the integrated area under the mean liver % ID time curve (AUC) was calculated.

For the 5 min. time period, the $1/T_1$ proton relaxation rate of the excised liver was measured at 20MHz and 37° C. as described above. Higher $1/T_1$ values are associated with greater MRI signal intensity on $T_1$-weighted images and are due to greater liver uptake of the agent and/or greater relaxivity in the microenvironments of the liver. Results are summarized in TABLE 2.

TABLE 2

Uptake and Induced Proton Relaxation Rates in Rat Liver

| DTPA derivative | Area under the % inj. dose in rate liver vs time curve (AUC) from 0 to 30 min* | $1/T1$ of excised rat liver 5 min. post-inj. ($s^{-1}$; 20 MHz, 37° C.)* |
|---|---|---|
| DTPA (R = R' = H) | 35 (n = 9) | 4.64 ± 0.16 (n – 3) |
| BOPTA (R = H, R' = BnOCH$_2$) | nd | |
| R (R' = H) | | |
| 1-(benzyl) | 213 (n = 9) | nd |
| 2-(benzyl) | nd | nd |
| 1-(phenylethyl) [CH2CH2Ph] | nd | nd |
| 1-(p-ethoxybenzyl) [EOP-DTPA] | 408 (n = 9) | 10.1 ± 1.5 (n = 3) |
| 1-(p-ethylbenzyl) | 469 (n = 10) | 12.3 ± 0.9 (n = 3) |
| 1-(p-isopropylbenzyl) | 400 (n = 8) | 10.9 ± 1.2 (n = 3) |
| 1-(p-n-butylbenzyl) [MS-264] | 491 (n = 6) | 14.6 ± 0.2 (n = 2) |
| 1-(2,4-di-Me-benzyl) | 404 (n = 7) | 10.2 ± 0.6 (n = 3) |
| 1-(2,4,6-tri-Me-benzyl) | 408 (n = 7) | 11.7 ± 0.6 (n = 3) |
| 1,3-dibenzyl | 254 (n = 9) | 8.40 (n = 1) |
| 1,4-dibenzyl | 378 (n = 3) | 8.66 (n = 1) |
| 1-(p-ethylbenzyl)-3-benzyl | nd | nd |
| 1,3-di(p-ethylbenzyl) | 260 (n = 3) | 11.2 (n = 1) |
| 1-(p-n-butylbenzyl)-3-benzyl | 313 (n = 3) | 13.0 (n = 1) |

*(Total number of animals in experiment listed as "n")

Rabbit liver uptake

Figure 1:
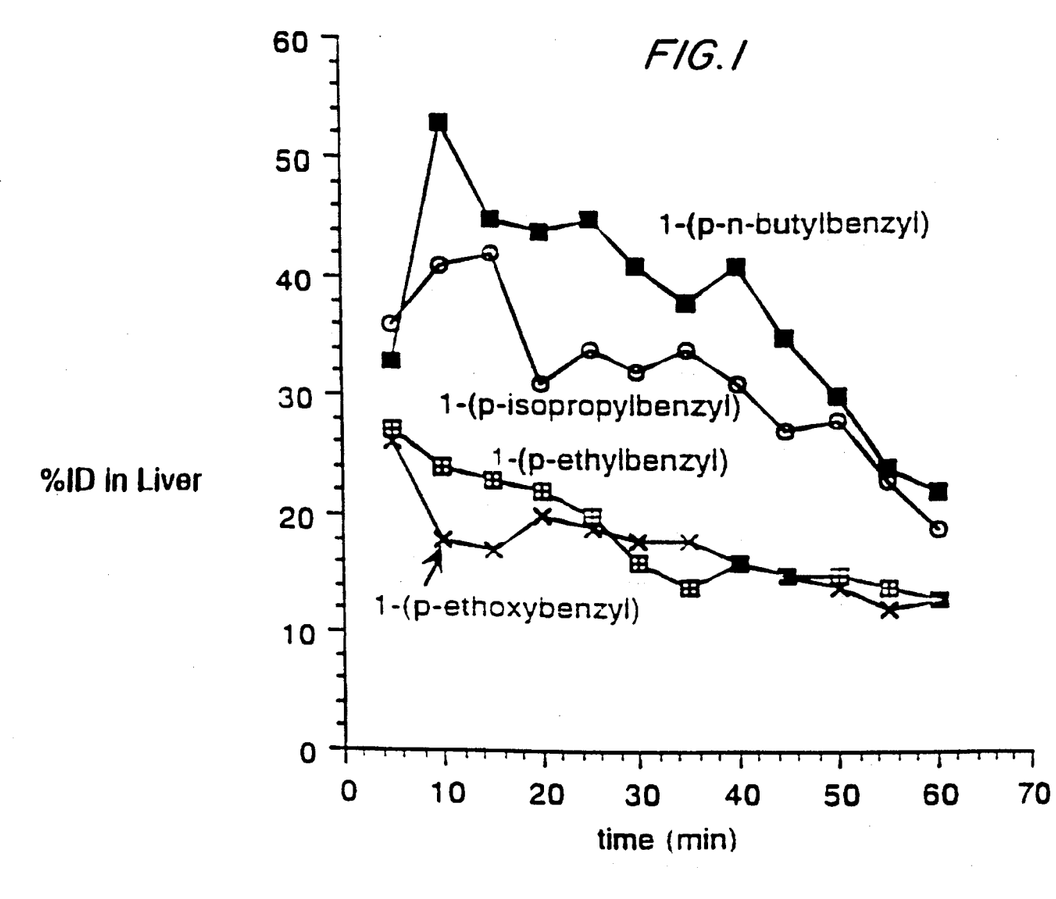
FIG. 1 is a graphical representation of experimental data taken from liver uptake studies performed on rabbits comparing 1-(p-n-butylbenzyl) diethylenetriamine pentaacetic acid to structurally similar contrast agents.

Anesthetized (pentobarbital, 35 mg/kg, ip.) adult rabbits (2.5–4 kg) were administered 50 μmol/kg of a $^{153}$Gd-labeled chelate (approximately 30 μCi/kg) via a cannulated marginal ear vein. Rabbits (1 per compound) were positioned supine under a gamma camera set with a photo peak energy of 100 keV +/– 20% and equipped with a low energy parallel hole collimator. Immediately after chelate administration, dynamic planar whole body scintigraphy was performed every five minutes for at least one hour. Images were acquired in a 64×64 matrix, and region of interest (ROI) analysis was performed using the Image 1.52 software package (National Institutes of Health). Percent injected does (% ID) in the liver at 5 min. intervals was calculated by dividing the counts in the liver ROI by the total counts in the body. Results are summarized in TABLE 3 and FIG. 1.

TABLE 3

| R | Area under the % inj. dose in rabbit liver vs time curve (AUC) 0 to from 30 min (n = 1 rabbit per cmpd) |
|---|---|
| 1-(p-ethoxybenzyl) [EOP-DTPA] | 480 |
| 1-(p-ethylbenzyl) | 553 |
| 1-(p-isopropylbenzyl) | 910 |
| 1-(p-n-butylbenzyl) [MS-264] | 1120 |

Monkey liver Uptake

Figure 2:
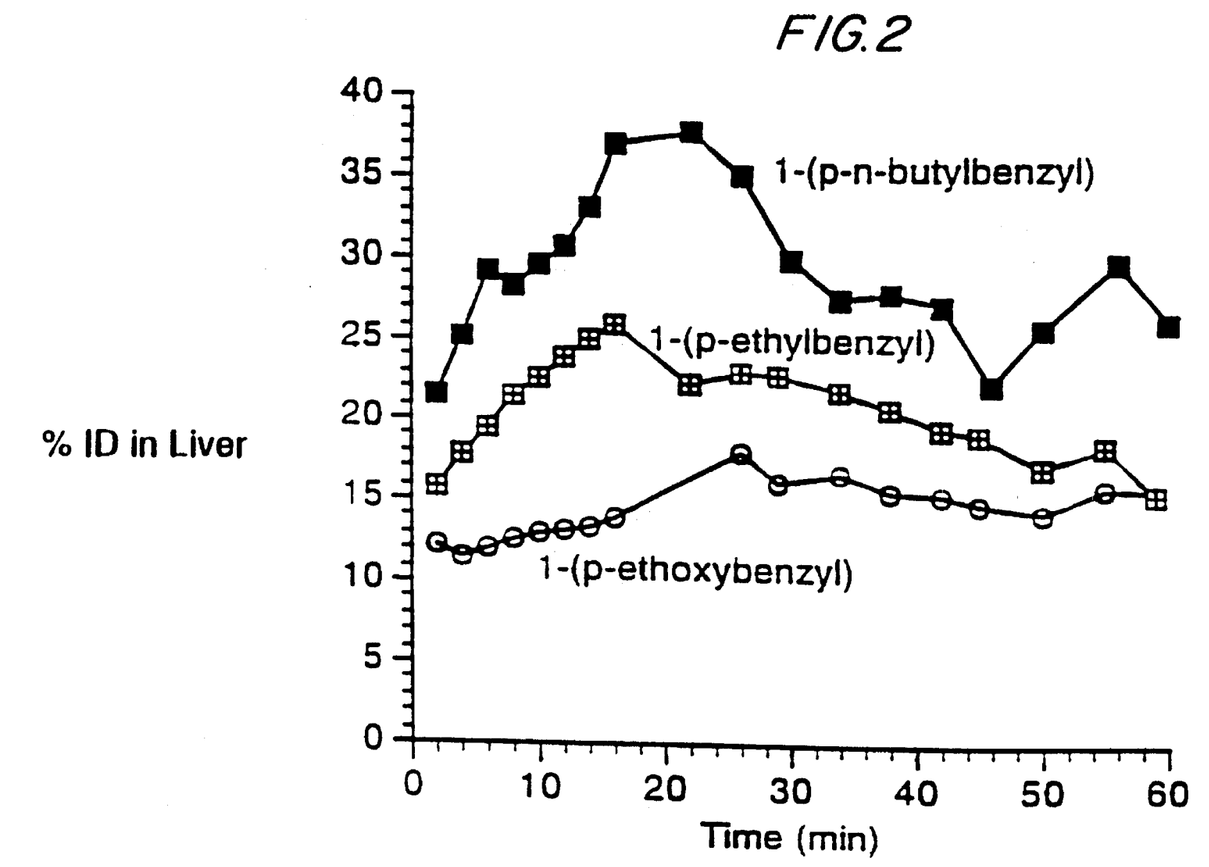
FIG. 2 is a graphical representation of experimental date taken from liver uptake studies performed on a monkey comparing 1-(p-n-butylbenzyl) diethylenetriamine pentaacetic acid to structurally similar contrast agents.
Figure 3:
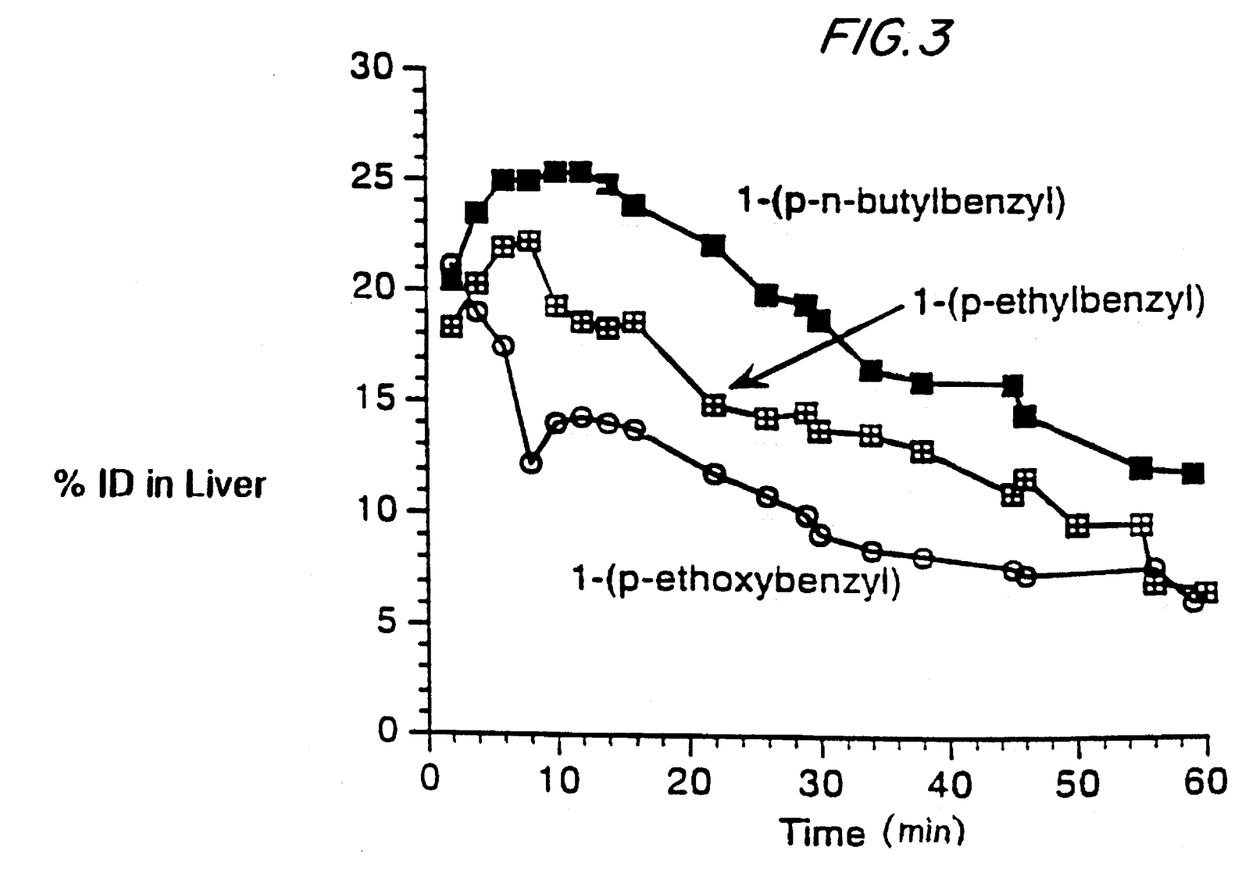
FIG. 3 is a graphical representation of experimental date taken from liver uptake studies performed on a second monkey comparing 1-(p-n-butylbenzyl) diethylenetriamine pentaacetic acid to structurally similar constrast agents.

Two adult male cynomolgus monkeys were scintigraphically imaged after iv. administration of 50 μmol/kg of the chelates labeled with $^{153}$Gd (approximately 40 μCi/kg). All agents were given to each monkey on separate days. Monkeys were anesthetized with ketamine hydrochloride (i.m., to effect), intubated and maintained on isoflurane (0.5–2%) and positioned supine under a gamma camera prior to compound administration. Images were acquired and analyzed as described above. Results are summarized in TABLE 4 and FIGS. 2 and 3.

TABLE 4

| | Area under the % inj. dose in monkey liver vs time curve (AUC) from 0 to 30 min | |
|---|---|---|
| R | Monkey #1 | Monkey #2 |
| 1-(p-ethoxybenzyl) [EOB-DTPA] | 396 | 380 |
| 1-(p-ethylbenzyl) | 617 | 494 |
| 1-(p-n-butylbenzyl) [MS-264] | 912 | 643 |

Biliary excretion in monkeys

Two adult male cynomolgus monkeys used for scintigraphic imaging were injected on different days with iv bolus of 50 μmol/kg of the chelates labeled with $^{153}$Gd (approximately 40 μCi/kg). Following completion of the imaging study, the animals were placed in metabolic cages and their total urine void and excreted feces were measured using a gamma counter at 24 and 48 hr post compound administration. The average recovery of activity was 68% of the injected dose. Results are summarized in TABLE 5.

TABLE 5

| R | % of recovered activity in feces in (biliary excretion) of monkeys over 48 hr (n = 2) |
|---|---|
| 1-(p-ethoxybenzyl) [EOB-DTPA] | 35 ± 3% |
| 1-(p-ethylbenzyl) | 48 ± 10% |
| 1-(p-n-butylbenzyl) [MS-264] | 86 ± 5% |

Synthesis of MS-264

α-Chloro-β-p-n-butylphenylpropionitrile (2)

One and a half moles (237 mL) of 4-n-butylaniline was dissolved in acetone (1500 mL). The solution was cooled to 10° C. and water (150 mL) and concentrated aqueous HCl (300 mL) were added. Sodium nitrite (69.0 g, 1.73 moles) in water (200 mL) was added dropwise to the cooled solution. The solution was adjusted to pH 4 by addition of solid sodium acetate. Acrylonitrile (148 mL, 2.25 moles) was added, followed by $CuCl_2 \cdot 2H_2O$ (38.4 g) in 50 mL $H_2O$. The reaction mixture was heated to 40° C. and was stirred at this temperature for 3 h. The aqueous layer was extracted with ether. The combined organics were washed with water and saturated aqueous $NaHCO_3$, were dried over $Na_2SO_4$, filtered and concentrated under reduced pressure. The residue was fractionally distilled at reduced pressure. The product was collected at 115°–130° C. @2 mm Hg, as 166.3 g (50% yield) of an orange oil.

α-Chloro-β-p-n-butylphenylpropionic Acid (3)

The α-chloro-β-p-butylphenylpropionitrile 2 (166 g, 0.750 moles) was stirred over 240 mL formic acid and 160 mL concentrated HCl at reflux for 16 h. The reaction mixture was cooled, diluted with 300 mL water and washed with ethyl acetate. The ethyl acetate solution was washed with water, saturated aqueous NaCl, dried over $Na_2SO_4$, filtered and concentrated under reduced pressure. The bulk oil solidified on standing. The solid was recrystallized twice from hexane, yielding 139.0 g (0.58 moles, 77% yield) of a white solid, mp. 52.7°–53.6° C.

p-n-Butylphenylalanine (4)

α-Chloro-β-p-butylphenylpropionic acid 3 (128 g, 0.534 moles) was suspended in 800 mL 30% aqueous ammonia. The reaction was stirred for 4 days at 40° C. in a tightly stoppered flask. After cooling to room temperature, the precipitate was removed by filtration through a coarse glass frit. The solid was washed thoroughly with ethanol followed by diethyl ether. The solid was dried under vacuum yielding 54.3 g (0.245 moles, 46% yield) of p-butylphenylalanine as a white solid. The solid was recrystallized from 2N HCl to give a white solid, mp 218°–223° C.

p-n-Butylphenylalanine Methyl Ester Hydrochloride

Butylphenylalanine 4 (4.20 g, 19.0 mmoles) was suspended in 50 mL dry methanol. The solution was saturated with HCl gas and was refluxed for 2 hours. The solution was cooled and then added to 400 mL diethyl ether. The resulting solid was collected by vacuum filtration and was washed with ether. The solid was redissolved in a minimum volume of methanol and precipitated in ether as before resulting in 3.45 g (12.7 mmoles, 67% yield) of white solid (mp 164.5°–165.1° C.).

p-n-Butylphenylalanine Ethylenediamine Amide (6)

Butylphenylalanine methyl ester hydrochloride 5 (3.45 g, 12.7 mmoles) was dissolved in 65 mL ethylenediamine and was stirred at room temperature for 16 h. The ethylenediamine was removed by evaporation at reduced pressure. The residue was partitioned between 1N NaOH and ethyl acetate and the aqueous was washed three times with ethyl acetate. The combined organic solutions were dried over $Na_2SO_4$, filtered and concentrated yielding 2.76 orange oil (83% yield). $^1H$ NMR ($CDCL_3$) δ7.50 (br. s, 1H), 7.15 (s, 4H), 3.60 (dd, 1H), 3.38–3.17 (3H), 2.85–250 (5H), 1.58 (m, 2H), 1.42–1.24 (6H), 0.93 (t, 3H).

1-p-n-Butylbenzyldiethylenetriamine Trihydrochloride (7)

Butylphenylalanine ethylenediamine amid 6 (2.76 g, 10.5 mmoles) was dissolved in 50 mL THF. Borane•THF (50 mL, 1.0M) was added slowly to the stirred solution. The reaction was then refluxed under argon for 16 h, and quenched by careful addition of methanol. The reaction mixture was concentrated under reduced pressure. Dry ethanol (75 mL) was added and the solution was saturated with HCl gas at 0° C. The mixture was brought to reflux for 24 h, after which the solution was cooled and concentrated. Ethyl ether was added to the concentrated solution and the resulting precipitate was collected by vacuum filtration and washed with ether, yielding 3.45 g (9.6 mmoles, 92%) white solid. Analysis calc'd for $C_{15}H_{27}N_3 \cdot 3HCl$: C, 50.22; H, 8.43; N, 11.71; Cl, 29.64 found: C, 50.16; H, 8.44; N, 11.76; Cl, 29.57.

1-p-n-Butylbenzyldiethylenetriamine penta-t-butyl Acetate (8)

Butylbenzyldiethylenetriamine trihydrochloride 7 (3.45 g, 9.62 mmoles) was suspended in 50 mL dry DMF. Diisopropylethylamine (25 mL, 144 mmoles) was added followed by 12.5 mL (77 mmoles) t-butylbromoacetate. The reaction was stirred at room temperature for 16 h under argon. The DMF and excess reagents were removed by evaporation under reduced pressure. The residue was partitioned between concentrated aqueous $NaHCO_3$ and chloroform. The organic solution was washed once each with water and saturated aqueous NaCl, dried over $Na_2SO_4$, filtered and concentrated under reduced pressure. The crude product was filtered through silica gel in 1:1 ethyl acetate: hexane. After being reconcentrated, the product was obtained as 6.88 g (8.39 mmol, 87% yield) of a light yellow oil. $^1H$ NMR ($CDCl_3$) δ 7.15 (d, 2H), 7.04 (d, 2H), 3.50–3.35 (10H), 3.09 (m, 1H), 2.83 (m, 2H), 2.75–245 (8H), 1.65–1.10 (49H), 0.94 (t, 3H).

1-p-n-Butylbenzyldiethylenetriamine Pentaacetic acid (9)

The penta-t-butyl ester 8 (6.88 g, 8.39 mmol) was dissolved in 1:1 dioxane:concentrated HCl and was stirred at room temperature for 16 h. The reaction mixture was concentrated under reduced pressure yielding the crude product as 4.79 g of a tan foam. The product was eluted from a 10 g C-18 Sep-Pak cartridge with 40% aqueous acetonitrile. The acetonitrile was evaporated and the resulting aqueous solution was lyophilized producing 3.30 g (6.12 mmoles, 73% yield) of a flocculent white solid. Analysis calc'd for $C_{25}H_{37}N_3O_{10}$: C, 55.65; H, 6.91; N, 7.79; found: C, 55.06; H, 6.99; N, 7.71; Cl, 0.00.

Gadolinium(III) 1-(p-n-butylbenzyl) diethylenetriamine pentaacetate dimeglumine salt (10)

Gadolinium oxide (1.99 g, 5.5 mmol), 1-(p-nbutylbenzyl)diethylenetriamine pentaacetic acid 9(6.00 g, 10.0 mmol [90% by weight]) and N-methyl-D-glucamine (3.90 g, 20 mmol) were weighed in a 100-mL round-bottom flask and 30 mL of distilled water was added to it. The mixture was stirred at 95° C. for six hours. The resulting cloudy solution was loaded on a 10-g C-18 Sep-Pak® cartridge and the complex was eluted with water. The solvent was removed on a rotary evaporator, the resulting white solid residue was dried in high vacuo for 24 hours at 45° C. Yield: 9.78 g (88%). Anal. Calcd for $C_{39}H_{70}GdN_5O_{21}$: C, 42.50; H, 6.40; N, 6.35; Gd, 14.27. Found: C, 42.11; H, 6.08; N, 6.35; Gd, 14.03.

We claim:

1. A complex of a paramagnetic metal and 1-(p-n-butylbenzyl)diethylenetriamine pentaacetic acid and pharmaceutically acceptable salts thereof.

2. The complex according to claim 1, wherein the paramagnetic metal is selected from the group consisting of Gd(III), Fe(III), Mn(II), Mn(III), Cr(III), Cu(II), Dy(III), Tb(III), Ho(III), Er(III) and Eu(III).

3. The complex according to claim 1, wherein the paramagnetic metal is Gd(III).

4. Gadolinium(III) -1-(p-n-butylbenzyl) diethylenetriamine pentaacetate dimeglumine salt.

5. The complex according to claim 1 wherein 1-(p-n-butylbenzyl)diethylenetriamine pentaacetic acid is present in racemic form.

6. The complex according to claim 1 wherein 1-(p-n-butylbenzyl)diethylenetriamine pentaacetic acid is present enantiomerically enriched or enantiomerically pure form.

7. A pharmaceutical composition comprising a compound according to any one of claims 1 to 6 together with a pharmaceutically acceptable carrier, adjuvant or vehicle.

8. The pharmaceutical composition according to claim 7, further comprising a free organic ligand or a pharmaceutically acceptable salt thereof.

9. The pharmaceutical composition according to claim 7, further comprising a free organic ligand or calcium, sodium, meglumine or combination salts thereof.

10. The pharmaceutical composition according to claim 8, wherein the organic ligand is 1-(p-n-butylbenzyl) diethylenetriamine pentaacetic acid.

11. A method for tissue-specific contrast enhancement of MR images of mammalian organs and tissues comprising the step of administering a diagnostically effective amount of a complex according to any one of claims 1 to 6.

12. The method according to claim 11 for contrast enhancement of MR images of the hepatobiliary system.

13. Use of a compound according to any one of claims 1 to 6 for the manufacture of a MRI contrast agent.

14. A method for tissue-specific diagnostic X-ray imaging of mammalian organs and tissues comprising the step of administering a diagnostically effective amount of a complex according to any one of claims 1 to 6.

15. The pharmaceutical composition according to claim 9, wherein the organic ligand is 1-(p-n-butylbenzyl) diethylenetriamine pentaacetic acid.

\* \* \* \* \*

UNITED STATES PATENT AND TRADEMARK OFFICE
CERTIFICATE OF CORRECTION

PATENT NO. : 5,582,814
DATED : December 10, 1996
INVENTOR(S) : Scott et al.

It is certified that error appears in the above-indentified patent and that said Letters Patent is hereby corrected as shown below:

Column 7, line 45, "diethylenetraimine" should read -- diethylenetriamine --.

Column 13, line 21, "amid" should read amide --.

Signed and Sealed this

Eighth Day of April, 1997

Attest:

BRUCE LEHMAN

Attesting Officer

Commissioner of Patents and Trademarks